United States Patent [19]

Gerz

[11] Patent Number: 5,691,474
[45] Date of Patent: Nov. 25, 1997

[54] METHOD AND APPARATUS FOR DYNAMIC DETERMINATION OF THE THICKNESS AND/OR BASIS WEIGHT OF MOVING MATERIAL UNDER TEST

[75] Inventor: Christoph Gerz, Ottering, Germany

[73] Assignee: Giesecke & Devrient GmbH, Munich, Germany

[21] Appl. No.: 575,366

[22] Filed: Dec. 20, 1995

[30] Foreign Application Priority Data

Dec. 23, 1994 [DE] Germany .............. 44 46 367.7

[51] Int. Cl.[6] .................................................. G01N 29/00
[52] U.S. Cl. ........................... 73/580; 73/159; 73/627; 73/597
[58] Field of Search ............................. 73/573, 580, 597, 73/627, 644, 159, 596, 598

[56] References Cited

U.S. PATENT DOCUMENTS

| | | | |
|---|---|---|---|
| 3,470,734 | 10/1969 | Agdur et al. | 73/580 |
| 3,562,500 | 2/1971 | Grant | 73/159 |
| 3,757,122 | 9/1973 | Bossen | 73/159 |
| 4,446,735 | 5/1984 | Weilacher | 73/597 |
| 4,519,249 | 5/1985 | Hunt | 73/627 |
| 4,612,807 | 9/1986 | Wunderer | 73/580 |
| 4,991,432 | 2/1991 | Houghton et al. | 73/159 |

OTHER PUBLICATIONS

W. Manthey und N. Kroemer, *Technisches Messen tm 56 (1989) 10*, "Ultraschallsensoren auf der Basis piezoelektrischer Polymere", pp. 377–384.

Wolfgang Manthey und Valentin Mágori, *Sensor 1993, Kongressand II*, "Ultraschallwandler–Arrays für Anwendungen in Luft", pp. 81–88.

*Primary Examiner*—Hezron E. Williams
*Assistant Examiner*—Helen C. Kwok
*Attorney, Agent, or Firm*—Hazel & Thomas, P.C.

[57] ABSTRACT

The invention relates to a method and apparatus for dynamic determination of the thickness and/or basis weight of moving material under test. The material under test is exposed to a focused ultrasound filed with high sound intensity, whereby the sound fraction coming from the material under test is detected directly in the near filed, i.e. at a distance smaller than or equal to the acoustic wavelength used, and evaluated for determining the thickness and/or basis weight. The near-field measurement preferably takes place with continuous sound and in transmission.

9 Claims, 2 Drawing Sheets

METHOD AND APPARATUS FOR DYNAMIC DETERMINATION OF THE THICKNESS AND/OR BASIS WEIGHT OF MOVING MATERIAL UNDER TEST

BACKGROUND OF THE INVENTION

This invention relates to a method for dynamic noncontacting determination of the thickness and/or basis weight of a material under test, such as bank notes, paper or the like, transported in a defined direction, by means of ultrasound, and to an apparatus for carrying out the method.

A method of this type is known, for example, from EP-B1 0 167 010. A sound transmitter radiated ultrasonic waves onto the moving material under test, whereby a portion of ultrasonic waves coming from the material under test is detected by a receiver in the form of a reflection or transmission measurement. The detected sound intensity is evaluated as a measure for determining thickness and/or basis weight. Due to diffraction effects, is known method can only be used to recognize structures on the material under test which have an extent above one wavelength.

The prior art furthermore shows ultrasound sensors based on piezoelectric polymer files, such as for identification or orientation functions. As an example, reference is made to the articles by W. Manthey and N. Kroemer "Technisches Messen" tm 56 (1989) 10, R. Oldenbourg-Verlag, and W. Manthey, Valentin Mágori "Sensor 93, Kongressband II". These articles describe ultrasound transducer arrays containing a plurality of transmitters in the form of cylindrically arched piezopolymer films which are disposed in a plane.

OBJECT OF THE INVENTION

The problem underlying the invention is to propose a method and apparatus for determining the thickness and/or basis weight of material under test which involve little technical effort while permitting high spatial resolution in the measuring plane and a good signal field.

This problem is solved according to the invention by the features stated in the characterizing parts of the independent claims.

SUMMARY OF THE INVENTION

The basic idea of the invention is to expose the material under test to a focused ultrasound filed with high sound intensity and to detect the portion of the ultrasonic waves coming through the material under test directly in the near filed, i.e. at a distance smaller than or equal to the acoustic wavelength used, and to evaluate it for determining thickness and/or basis weight. The focusing of the sound field is obtained by spatially arranging a plurality of transmitter elements in such a way that they are all the same distance away from the measuring point and the transmitter elements radiate sound waves in phase whose amplitudes are superimposed at the measuring point. This focuses the sound at the measuring point.

The invention has the advantage that the spatial arrangement of the transmitter elements achieves the focusing with little technical effort. Furthermore the signal-to-noise ratio is increased by the focusing at a constant background noise compared to nonfocusing methods. Simultaneously, the portion of the ultrasonic waves that does not contribute to measurement and that can pass to the receiver in uncontrolled ways is reduced.

The near-field measurement preferably takes place with continuous portion of and in transmission, i.e. only the sound the ultrasonic waves passing through the material under test is detected and taken as the basis for evaluation. The use of continuous sound permits continuous scanning in the moving direction of the material under test. The material under test is preferably exposed to a focused linear sound field over the entire width, whereby the material under test moving in the longitudinal direction can then also be scanned perpendicular to the moving direction of the material and thus completely. This permits, for example, the ascertainment of adhesive strips on bank notes, or missing parts on bank notes, or also the detection of so-called double and multiple pulls, which is important for counting in bank note sorting machines.

The transmitter elements are preferably disposed on a carrier corresponding in shape to a segment of a cylinder envelope, and are formed substantially of semicylindrically arched piezopolymer films. To permit high spatial resolution and a good signal yield, the dimensions of the sound-sensitive receiver surface must be smaller than one wavelength. The inventive receiver, which has a small tube for feeding sound for capturing the portion of the ultrasonic waves coming from the material under test and conducting it to a microphone in the manner of a stethoscope, allows resonances to be avoided between the material under test, on the one hand, and the receiver and its mounting, on the other hand.

The small tube can be filled on the outside with a highly sound-absorbent material and on the inside completely or partly with a moderately sound-absorbent material. The latter avoids resonances in the tube, and the foam inside the tube can also protect the microphone from soiling. The use of the tube thus permits the receiver side including the sound-sensitive surface to be lined almost completely with foam. The diameter of the tube is adapted accordingly to the active surface of the receiver. One preferably uses a piezofilm microphone which can readily be coupled acoustically to the tube and whose active surface can be realized with an extent of less than one wavelength.

Further advantages and developments of the invention can be found in the subclaims as well as in the following description of embodiments of the invention with reference to the enclosed figures, as described below.

DETAILED DESCRIPTION OF THE PREFERRED EMBODIMENTS

Figure 1:
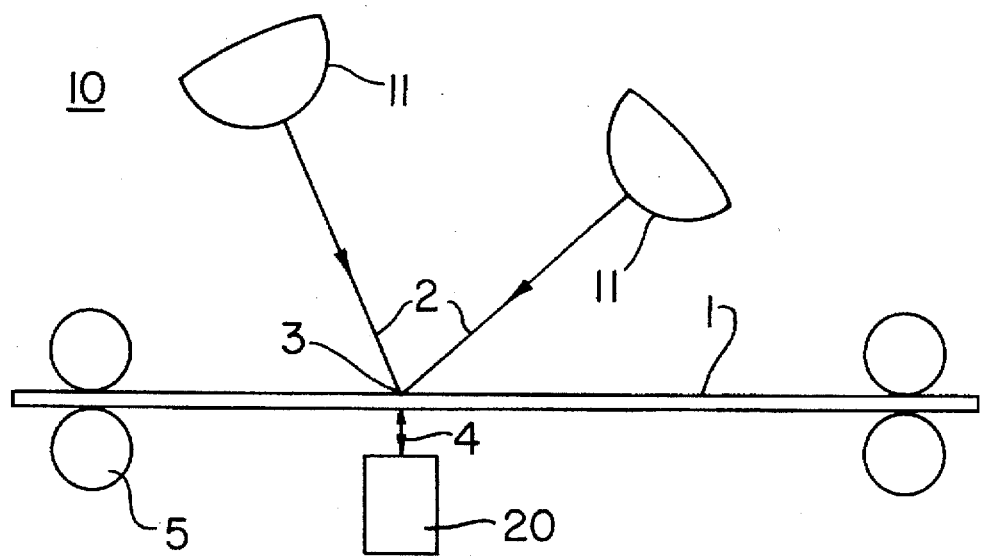
FIG. 1 shows a schematic representation of an apparatus for thickness and/or basis weight determination.

FIG. 1 shows by way of example a schematic representation of an apparatus for carrying out the inventive method. Material under test 1, e.g. a bank note, is moved through between transmitter array 10 and receiver 20 by transport device 5 indicated in the form of transport rolls. The transmitter array includes at least two transmitter elements 11 disposed relative to transport device 5 in such a way that the ultrasonic waves radiated by transmitter elements 11 in the direction of arrows 2 hit measuring point 3 on the same sound path 2, i.e. at the same distance, e.g. 20 mm, from said measuring points. At measuring point 3, the sound pressure amplitudes radiated by the transmitters sum up to a focused sound filed with high intensity. Transmitter elements 11 all have the same radiation characteristics and are operated synchronously, thereby guaranteeing in-phase radiation of sound waves with constant amplitude.

For determining thickness and/or basis weight, the sound fraction transmitted by the material under test is detected by the receiver array at distance 4, which is smaller than or equal to the acoustic wavelength used, and evaluated by a device not shown. To achieve high spatial resolution and a good signal yield, the dimensions of the sound-sensitive receiver surface must be smaller than the wavelength used. To avoid resonances between the test object, on the one hand, and the receiver and its mounting, on the other hand, the receiver can be embedded in a sound-absorbent foam, as described in the following. If the transmitter and receiver are embedded accordingly, the invention can also be sued in principle for reflection measurement, as described for example in the abovementioned EP-B1 0 167 010.

Figure 2:
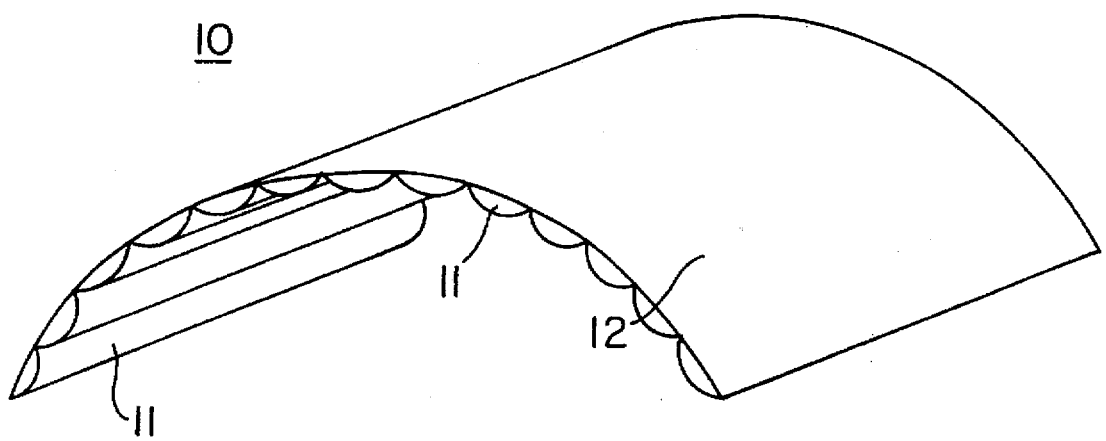
FIG. 2 shows an embodiment of a transmitter array.

FIG. 2 shows an embodiment of a transmitter array for an apparatus according to FIG. 1. Transmitter array 10 includes a plurality of transmitter elements 11 which contain substantially semicylindrically arched piezopolymer films disposed side by side on the concave side of carrier 12. The piezopolymer films all have the same geometry and the same material properties, so that the same radiation characteristic is obtained for all transmitter elements. For fastening the piezopolymer films, carrier 12 can be provided with grooves in which the piezopolymer films are clamped. The carrier corresponds in shape e.g. to a segment of a cylinder envelope. Due to the piezopolymer films disposed on the cylinder envelop of carrier 12 the radiated ultrasonic waves are focused in the direction of the cylinder axis over the entire length of the films, resulting in a linear sound field with high sound intensity. The geometry of the transmitter array, i.e. the length of the semicylindrical piezopolymer films, can be selected so that it corresponds for example, to the maximum width of a bank note. The transmitter array can be operated, for example, at a frequency of approximately 100 kHz. The fundamental requirements and laws for building up transmitter elements with piezopolymer films are stated in the abovementioned articles "Ultraschallsensoren auf der Basis piezoelektrischer Polymere" by W. Manthey and N. Kroemer, in Technisches Messen, tm 56 (1989) 10, R. Oldenbourg-Verlag, and "Ultraschallwandler-Arrays für Anwendungen in Luft" by W. Manthey and Valentin M agori, in SENSOR 93 Kongressband II, and will not be described here more closely.

Figure 3:
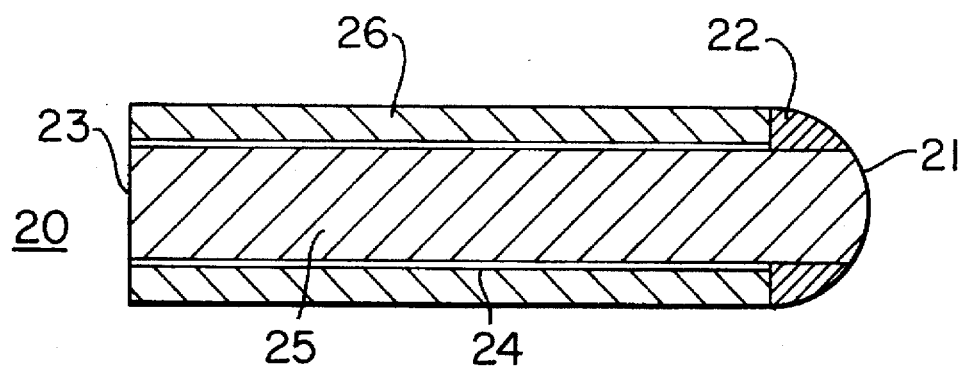
FIG. 3 shows an embodiment of a receiver.

FIG. 3 shows a sectional view of an embodiment of an ultrasound receiver which is preferably used with the transmitter array shown in FIG. 2. Receiver 20 includes at least one microphone 21, e.g. in the form of a piezopolymer film, which is disposed on the convex side of cylindrical carrier 22 flattened on one side. Carrier 22 has on the flattened side hole 23 for feeding the sound of the portion of the ultrasonic waves coming from the material under test. The dimensions of the microphone for operation at approximately 100 kHz are for example, 3.5 mm for the cylinder diameter at a film width of likewise 3.5 mm. Additionally, small tube 24 can be disposed directly on microphone 21 for capturing the portion of the ultrasonic waves coming from the material under test and for conducting it to the microphone in the manner of a stethoscope. The tube is provide don the outside with sound-absorbent foam 26, e.g. an open-pore polyurethane foam, whereby only the portion of the ultrasonic waves coming directly from the material under test is detected and no sound waves reflected by the receiver or the transmitter array, which could falsify the measurement, occur.

Furthermore, it is possible to fill the tube on the inside completely or partly with moderately sound-absorbent material 25 to avoid resonances in the tube and protect the microphone form soiling. The foam should absorb so much that no resonances occur, and pass so much that a sufficient signal is obtained. The tube can have e.g. an outside diameter of 3 mm and an inside diameter of 2.5 mm and a length of approximately 30 mm.

Figure 4:
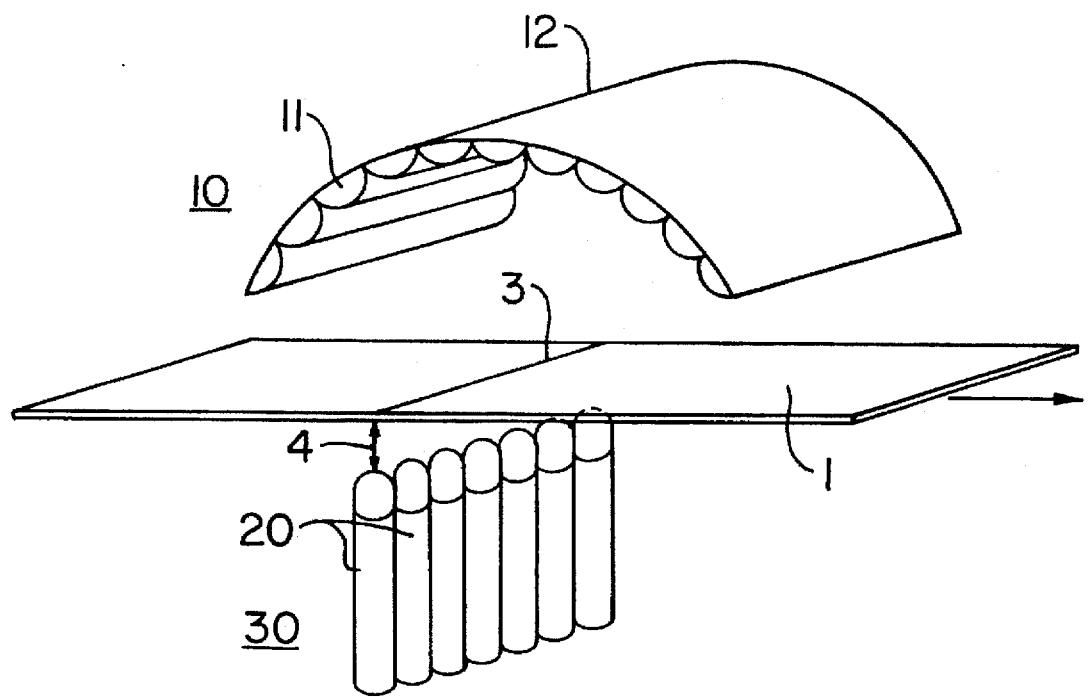
FIG. 4 shows a schematic representation of an apparatus having a receiver array with a plurality of receivers.

FIG. 4 shows a schematic representation of an apparatus having receiver array 30 with a plurality of receiver 20, which is advantageous in particular if measurement is to be done in a plurality of parallel tracks, e.g. over the entire band note width. Transmitter array 10 exposes material under test 1 to a focused linear sound field over entire width 3. The material under test moving in the longitudinal direction can then be completely scanned in a transmission measurement by receiver array 30 disposed perpendicular to the transport direction at the distance 4, e.g. 0.5 to 2 mm, and extending over the entire width of the material under test.

I claim:

1. A method for dynamic noncontacting determination of the thickness and/or basis weight of a material under test using ultrasound, the material under test being transported in a defined direction characterized in that a plurality of transmitters each with the same radiation characteristics radiate ultrasonic waves in phase toward a defined area of the material under test perpendicular to the transport direction, so that a focused sound field with high sound intensity is produced in the defined area of the material under test, a portion of the ultrasonic waves coming through the material under test being detected at a distance smaller than or equal to an acoustic wavelength of the ultrasonic waves, and the detected portion of the ultrasonic waves being evaluated for determining the thickness and/or basis weight.

2. The method of claim 1, characterized in that the material under test is moved in a longitudinal direction, and the defined area extends over an entire width of the material under test and is linear.

3. The method of claim 1, characterized in that the material under test is exposed to continuous sound and the portion of the ultrasonic waves coming through the material under test is detected and evaluated.

4. An apparatus for carrying out the method of claim 1, including means for transporting the material under test in the defined direction, a transmitter array, at least one receiver, characterized in that the transmitter array has the plurality of transmitters that radiate the focused sound field with high sound intensity onto the defined area of the material under test perpendicular to the transport direction, the transmitters all being disposed the same distance away from the defined area of the material under test exposed to the focused sound field, and the receiver being disposed a distance away from the material under test which is smaller than or equal to the acoustic wavelength used.

5. The apparatus of claim 4, characterized in that the transmitters of the transmitter array are substantially semicylindrically arched piezopolymer films with lengths corresponding at least to a width of the material under test.

6. The apparatus of claim 5, characterized in that the semicylindrically arched piezopolymer films are disposed in a row on a carrier which corresponds in shape to a segment of a cylinder envelope.

7. The apparatus of claim 4, characterized in that the apparatus has a plurality of receivers disposed side by side perpendicular to the transport direction as a receiver array which extends over an entire width of the material under test.

8. The apparatus of claim 7, characterized in that each of the receivers has a small tube for feeding sound.

9. The apparatus of claim 8, characterized in that each of the receivers has a substantially semicylindrically arched piezopolymer film disposed on one side of a carrier, and the carrier is provided with a hole for feeding sound.

* * * * *